(12) United States Patent
Zalipsky

(10) Patent No.: US 6,586,001 B1
(45) Date of Patent: Jul. 1, 2003

(54) NEUTRAL LIPOPOLYMER AND LIPOSOMAL COMPOSITIONS CONTAINING SAME

(75) Inventor: Samuel Zalipsky, Redwood City, CA (US)

(73) Assignee: Alza Corporation, Palo Alto, CA (US)

( * ) Notice: Subject to any disclaimer, the term of this patent is extended or adjusted under 35 U.S.C. 154(b) by 0 days.

(21) Appl. No.: 09/615,552

(22) Filed: Jul. 13, 2000

Related U.S. Application Data

(60) Provisional application No. 60/143,810, filed on Jul. 14, 1999.

(51) Int. Cl.[7] ............................................. A61K 9/127
(52) U.S. Cl. .................. 424/450; 242/1.21; 242/9.321; 242/9.51; 428/402.2
(58) Field of Search .................. 424/450, 1.21, 424/9.321, 9.51, 417, 94.3, 812; 436/829; 935/54; 428/402.2

(56) References Cited

U.S. PATENT DOCUMENTS

| | | |
|---|---|---|
| 5,741,518 A | 4/1998 | Ribier et al. |
| 5,786,387 A | 7/1998 | Watanabe et al. |
| 5,866,158 A | 2/1999 | Ribier et al. |
| 5,891,468 A | 4/1999 | Martin et al. |

FOREIGN PATENT DOCUMENTS

| | | |
|---|---|---|
| FR | 2 694 893 A | 2/1994 |
| WO | WO 96 10391 | 4/1996 |
| WO | WO 98/18480 | 5/1998 |

OTHER PUBLICATIONS

*U.S. Patents 5,866,158 and 5,741,518 submitted in lieu of FR 2 694 893 A.

Primary Examiner—Gollamudi S. Kishore
(74) Attorney, Agent, or Firm—Paul B. Simboli

(57) ABSTRACT

Liposomes containing PEG-substituted neutral lipopolymers provide similar circulation times to liposomes incorporating conventional, negatively charged PEG-substituted phospholipids. Use of the uncharged lipopolymers can also present advantages in terms of interactions with cell surfaces and reduced leakage of charged substances, particularly cationic drugs, from the liposomes. The lipopolymers are of the formula:

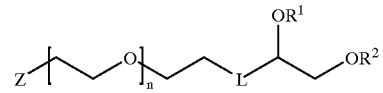

wherein each of $R^1$ and $R^2$ is an alkyl or alkenyl chain having between about 8 to about 24 carbon atoms, n is about 10 to about 300, Z is selected from the group consisting of hydroxy, alkoxy, benzyloxy, carboxylic ester, sulfonic ester, alkyl or aryl carbonate, amino, and alkylamino, and the linkage L is selected from the group consisting of (i) —X—(C=O)—Y—CH$_2$—, (ii) —X—(C=O)—, and (iii) —X—CH$_2$—, wherein X and Y are independently selected from oxygen, NH, and a direct linkage.

16 Claims, 8 Drawing Sheets

NEUTRAL LIPOPOLYMER AND LIPOSOMAL COMPOSITIONS CONTAINING SAME

CROSS-REFERENCE TO RELATED APPLICATION

The complete disclosure set forth in the U.S. provisional patent application entitled "Neutral Lipopolymer and Liposomal Compositions Containing Same," Ser. No. 60/143,810, filed with the United States Patent and Trademark Office on Jul. 14, 1999, is incorporated herein. The applications are commonly owned.

FIELD OF THE INVENTION

The present invention relates to PEG-substituted neutral lipopolymers and their use in extended circulating time liposomes. Liposomes containing these lipopolymers provide similar blood circulation times when compared with liposomes incorporating conventional, negatively charged PEG-substituted phospholipids.

BACKGROUND OF THE INVENTION

Liposomes are used for a variety of therapeutic purposes, and in particular, for carrying therapeutic agents to target cells by systemic administration of liposomal formulations of these agents. Advantageously, liposome-drug formulations offer the potential of improved drug-delivery properties, which include, for example, controlled drug release. An extended circulation time is often needed for liposomes to reach a target region, cell or site. In particular, this is necessary where the target region, cell or site is not located near the site of injection. For example, when liposomes are administered systemically, it is desirable to coat the liposomes with a hydrophilic agent, for example, a coating of hydrophilic polymer chains such as polyethylene glycol, (PEG) to extend the blood circulation lifetime of the liposomes. Such surface-modified liposomes are commonly referred to as "long circulating" or "sterically stabilized" liposomes.

The most common surface modification to a liposome is the attachment of PEG chains, typically having a molecular weight from about 1000 daltons (Da) to about 5000 Da, and to about 5 mole percent (%) of the lipids making up the liposomes (see, for example, *Stealth Liposomes*, CRC Press, Lasic, D. and Martin, F., eds., Boca Raton, Fla., (1995)), and the cited references therein. The pharmacokinetics exhibited by such liposomes are characterized by a dose-independent reduction in uptake of liposomes by the liver and spleen via the mononuclear phagocyte system (MPS), and significantly prolonged blood circulation time, as compared to non-surface-modified liposomes, which tend to be rapidly removed from the blood and accumulated in the liver and spleen.

The most commonly used and commercially available PEG-substituted phospholipids are based on phosphatidyl ethanolamine (PE), usually DSPE (distearoyl phosphatidyl ethanolamine), which is negatively charged at the polar head group. Negative surface charge in a liposome can be disadvantageous in some aspects, e.g. in interactions with cells (see, for example, Miller et al., *Biochemistry*, 37:12875–12883 (1998)), and in the delivery of cationic drugs, where leakage of the drug may occur (see, for example, Webb et al., *Biochim. Biophys. Acta*, 1372:272–282 (1998)).

Accordingly, it would be beneficial to provide uncharged PEG-derivatized lipids that incorporate efficiently into lipid bilayers and provide long blood circulation times to liposomes. Ideally, such lipids are of low toxicity and easily produced.

SUMMARY OF THE INVENTION

In one aspect, the present invention includes a liposomal composition having from about 1 mole percent to about 10 mole percent of a neutral lipopolymer wherein the neutral lipopolymer is represented by the formula:

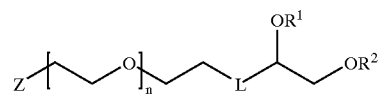

wherein:
each of $R^1$ and $R^2$ is an alkyl or alkenyl chain having between about 8 carbon atoms and about 24 carbon atoms;
n is between about 10 and about 300,
Z is selected from the group consisting of hydroxy, alkoxy, benzyloxy, carboxylic ester, sulfonic ester, alkyl or aryl carbonate, amino, and alkylamino; and
L is selected from the group consisting of (i) —X—(C=O)—Y—CH$_2$—, (ii) —X—(C=O)—, and (iii) —X—CH$_2$—, where X and Y are independently selected from oxygen, NH, and a direct linkage. Preferably, the composition includes from about 3 mole percent to about 6 mole percent of the neutral lipopolymer.

In another aspect, L is a hydrolyzable linkage such as a carbamate linkage, an ester linkage, or a carbonate linkage. In yet another aspect, Z is hydroxy or methoxy. Preferably, $R^1$ and $R^2$ are unbranched. In one aspect, $R^1$ and $R^2$ are both stearyl groups ($C_{17}H_{35}$). In another aspect, the value of n is preferably between about 20 and about 115, such that the molecular weight of the PEG group is between about 1000 Da to about 5000 Da.

The invention also provides a method for increasing blood circulation time of a liposome containing vesicle-forming lipids, by incorporating in the liposome about 1 mole percent to about 10 mole percent of a neutral lipopolymer having the formula as shown above. The invention further provides lipopolymers represented by this formula.

DETAILED DESCRIPTION OF THE INVENTION

I. Definitions

Figure 1:
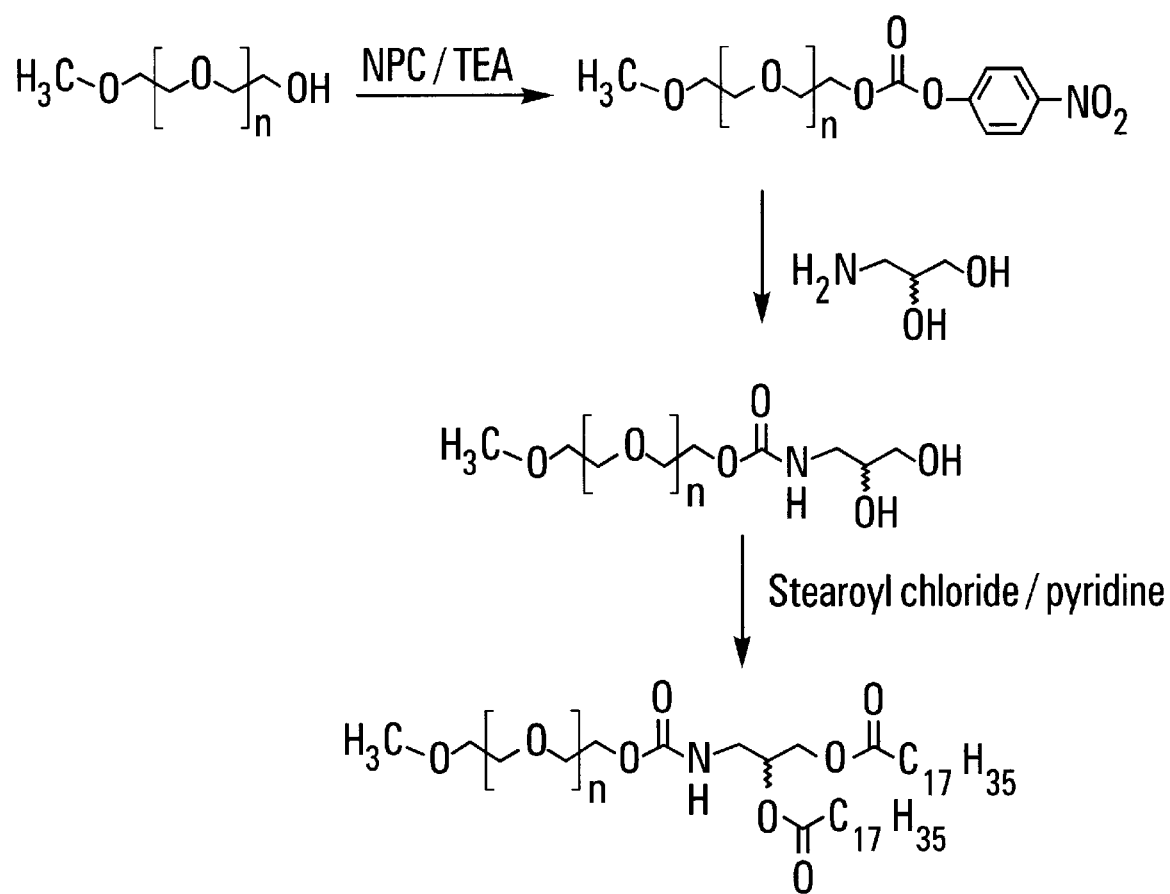
FIG. 1 shows a synthetic scheme for the preparation of a carbamate-linked uncharged lipopolymer, referred to herein as PEG-c-DS.

As used herein, the term "neutral" lipopolymer refers to a lipopolymer that is uncharged, i.e., having no ionic character. "Vesicle-forming lipids" refers to amphipathic lipids which have hydrophobic and polar head group moieties. Such vesicle-forming lipids can spontaneously form into bilayer vesicles in water as exemplified by phospholipids, or can be stably incorporated into lipid bilayers, wherein the hydrophobic moiety is in contact with the interior, i.e., one hydrophobic region of the bilayer membrane, and the polar head group moiety is oriented toward the exterior, i.e., the polar surface of the membrane. A class of vesicle-forming lipids of this type typically include one or two hydrophobic acyl hydrocarbon chains or a steroid group, and may contain a chemically reactive group, (such as an amine, acid, ester, aldehyde or alcohol) at the polar head group. Included in this class are the phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between from about 14 to about 22 carbon atoms in length, and have varying degrees of unsaturation. Other vesicle-forming lipids include glyco-lipids, such as cerebrosides and gangliosides, and sterols, such as cholesterol. For the compositions described herein, phospholipids, such as PC and PE, cholesterol, and the neutral lipopolymers described herein are preferred components.

"Alkyl" refers to a fully saturated monovalent radical containing carbon and hydrogen, which may be branched or a straight chain. Examples of alkyl groups are methyl, ethyl, n-butyl, t-butyl, n-heptyl, and isopropyl. "Lower alkyl" refers to an alkyl radical from about one to about six carbon atoms, as exemplified by methyl, ethyl, n-butyl, i-butyl, t-butyl, isoamyl, n-pentyl, and isopentyl.

"Alkenyl" refers to monovalent radical containing carbon and hydrogen, which may be branched or a straight chain, and contains at least one double bond.

Abbreviations: PEG: polyethylene glycol; MPEG: methoxy-terminated polyethylene glycol; Chol: cholesterol; PC: phosphatidyl choline; PHPC: partially hydrogenated phosphatidyl choline; PHEPC: partially hydrogenated egg phosphatidyl choline; HSPC: hydrogenated soy phosphatidyl choline; DSPE: distearoyl phosphatidyl ethanolamine; DSP or PEG-c-DS: distearoyl (carbamate-linked) PEG; APD: 1-amino-2,3-propanediol; DTPA: diethylenetetramine pentaacetic acid; Bn: benzyl.

II. Neutral Lipoplymers

The PEG-substituted neutral lipopolymers of the invention have the structure shown below:

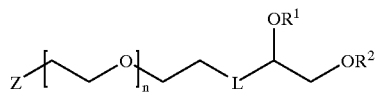

wherein:
  each of $R^1$ and $R^2$ is an alkyl or alkenyl chain having between about 8 to about 24 carbon atoms;
  n is between about 10 and about 300,
  Z is selected from the group consisting of hydroxy, alkoxy, benzyloxy, carboxylic ester, sulfonic ester, alkyl or aryl carbonate, amino, and alkylamino; and
  L is selected from the group consisting of (i) —X—(C=O)—Y—CH$_2$—, (ii) —X—(C=O)—, and (iii) —X—CH$_2$—, where X and Y are independently selected from oxygen, NH, and a direct linkage.

The lipopolymers include a neutral linkage (L) in place of the charged phosphate linkage of PEG-phospholipids, such as PEG-DSPE, which are frequently employed in sterically stabilized liposomes. This neutral linkage is typically selected from a carbamate, an ester, an amide, a carbonate, a urea, an amine, and an ether. Hydrolyzable or otherwise cleavable linkages, such as carbamates, carbonates, and esters, are preferred in applications where it is desirable to remove the PEG chains after a given circulation time in vivo. This feature can be useful in releasing drug or facilitating uptake into cells after the liposome has reached its target (Martin et al., U.S. Pat. No. 5,891,468; Zalipsky et al., PCT Publication No. WO 98/18813 (1998)).

The PEG group attached to the linking group preferably has a molecular weight from about 1000 Da to about 15000 Da; that is, where n is between about 20 and about 340. More preferably, the molecular weight is from about 1000 Da to about 12000 Da (n=about 20 to about 275), and most preferably between about 1000 Da to about 5000 Da (n=about 20 to about 115). $R^1$ and $R^2$ are typically from about 8 carbon atoms to about 24 carbon atoms, and are preferably between about 16 to about 20 carbons in length. Most preferably, $R^1=R^2\times C_{17}H_{35}$ such that COOR is a stearyl group.

As stated above, the incorporation of an uncharged lipid into a liposome can present significant advantages, such as reduced leakage of an encapsulated cationic drug. Additionally, another advantage is a greater flexibility in modulating interactions of the liposomal surface with target cells and with the RES (Miller et al., *Biochemistry*, 37:12875–12883 (1998)). PEG-substituted synthetic ceramides have been used as uncharged components of sterically stabilized liposomes (Webb et al., *Biochim. Biophys. Acta*, 1372:272–282 (1998)); however, these molecules are complex and expensive to prepare, and they generally do not pack into the phospholipid bilayer as well as diacyl glycerophospholipids.

The lipopolymers can be prepared using standard synthetic methods. For example, the carbamate-linked compound (L=—O—(C=O)—NH—CH$_2$—) is prepared, as shown in FIG. 1, by reacting the terminal hydroxyl of mPEG (methoxy-PEG) with p-nitrophenyl chloroformate to yield the p-nitrophenyl carbonate. This product is then reacted with 1-amino-2,3-propanediol to yield the intermediate carbamate. The hydroxyl groups of the diol are acylated to yield the final product. A similar synthesis, using glycerol in place of 1-amino-2,3-propanediol, can be used to produce a carbonate-linked product (L=—O—(C=O)—O—CH$_2$—). Preparation of carbamate-linked distearoyl and diecosanoyl lipopolymers is also described in Example 1.

Figure 2A:
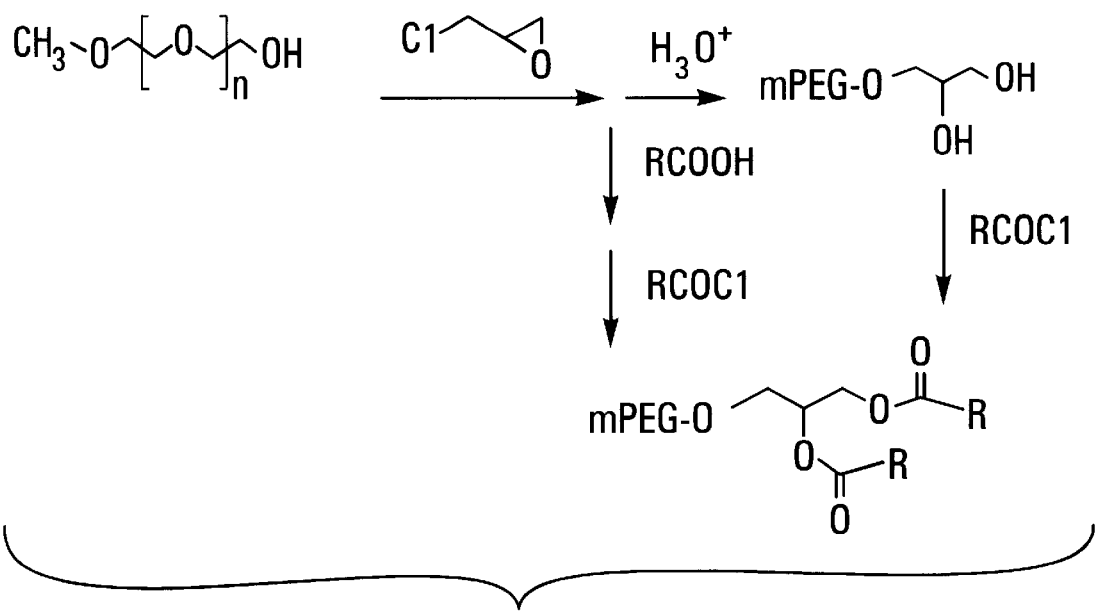
FIGS. 2A–2D show synthetic schemes for the preparation of ether-, ester-, amide-, and keto-linked uncharged lipopolymers.
Figure 2B:
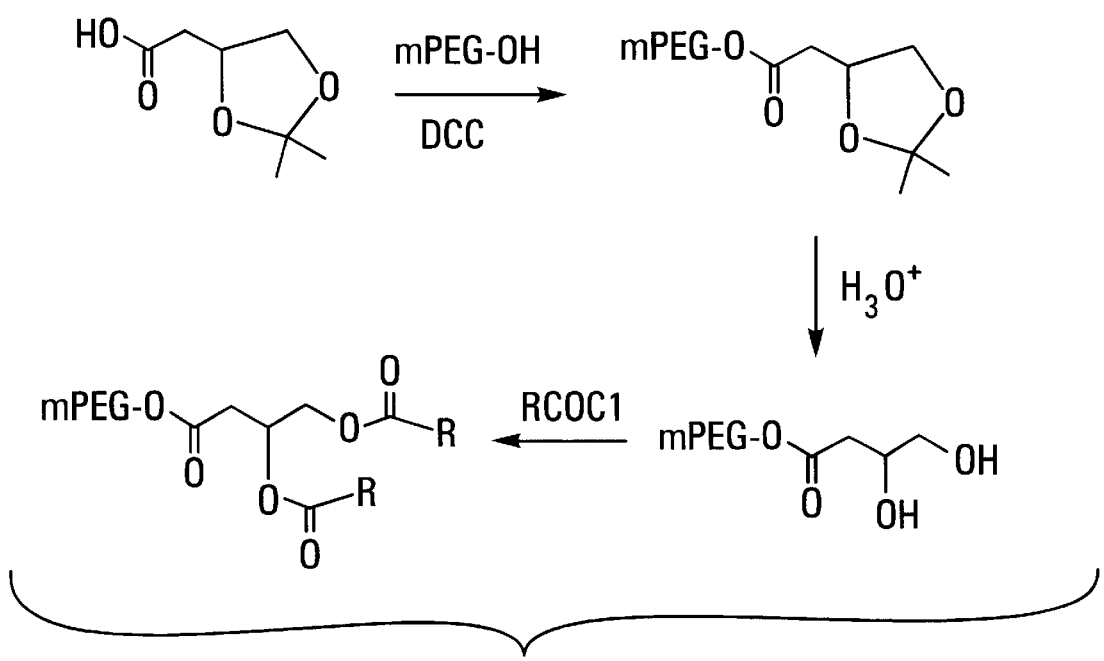

As shown in FIG. 2A, an ether-linked lipopolymer (L=—O—CH$_2$—) is prepared by reacting the terminal hydroxyl of mPEG-OH with glycidyl chloride, hydrolyzing the resulting epoxide, and acylating the resulting diol. Ester-linked lipopolymers (L=—O—(C=O)— or —O—(C=O)—CH$_2$—) can be prepared, for example, as shown to in FIG. 2B, by reacting mPEG—OH with an activated derivative of glyceric acid acetonide (2,2-dimethyl-1,3-dioxolane-4-carboxylic acid) or the four-carbon homolog, 2,2-dimethyl-1,3-dioxolane-4-acetic acid. The diol is then deprotected and acylated.

Corresponding reactions using mPEG-NH$_2$, prepared according to the method described in Zalipsky et al., PCT Publication No. WO 98/18813 (1998), in place of mPEG—OH, may be used to prepare lipopolymers having amide, urea or amine linkages (i.e., where L=—NH—(C=O)—NH—, —NH—(C=O)—CH$_2$—, —NH—(C=O)—NH—CH$_2$—, or —NH—CH$_2$—)

Figure 2C:
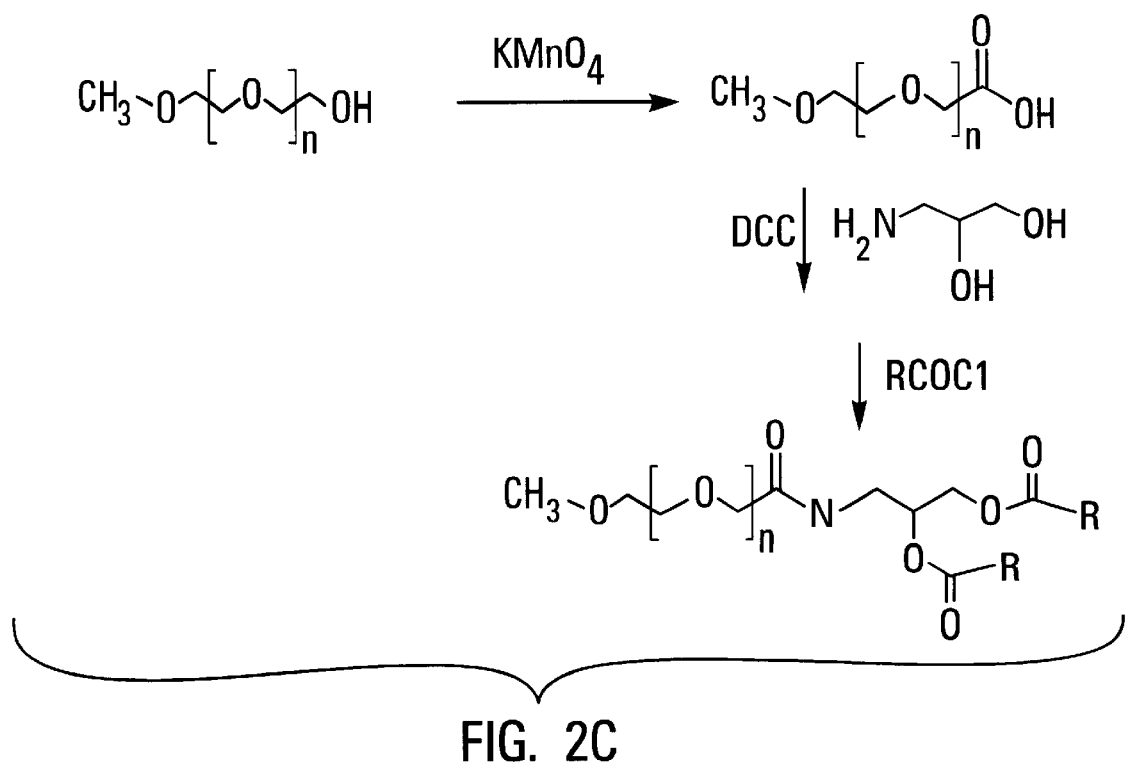
Figure 2D:
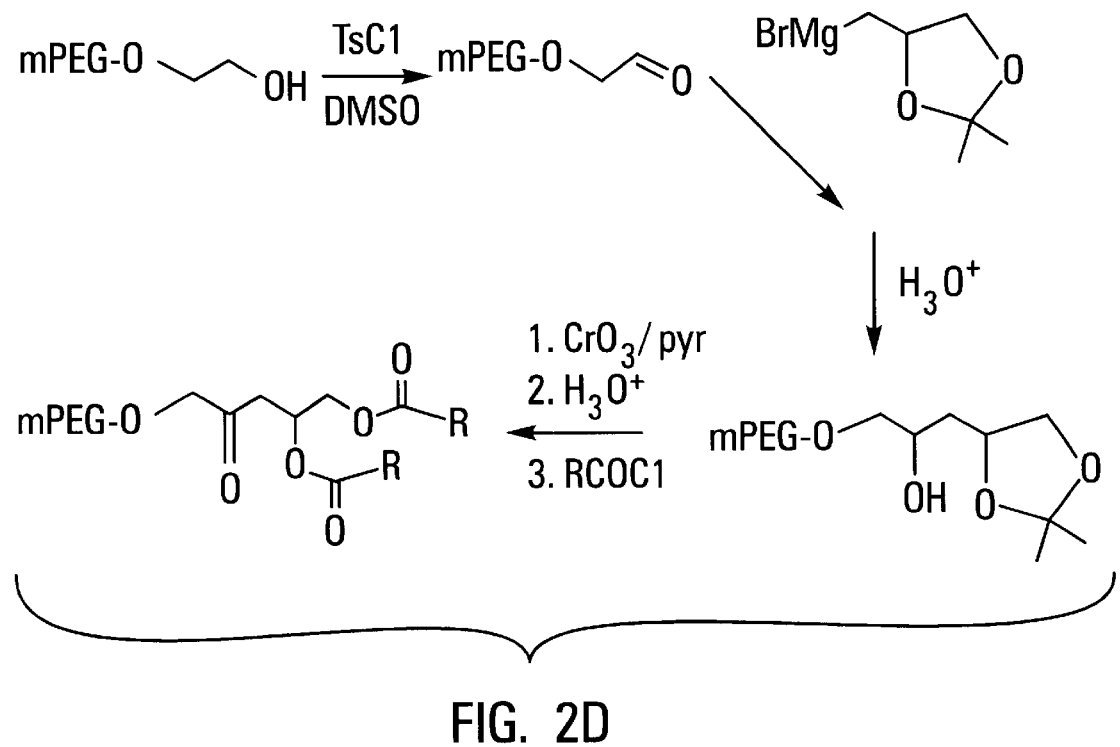

Compounds in which L is —X—(C=O)— where X is O or NH, can be prepared by reaction of an activated carboxyl-terminated PEG (prepared by oxidation of hydroxyl-terminated PEG and activation of the carboxyl group by, for example, conversion to the nitrophenyl ester or reaction with DCC) with 1,2,3-propanetriol or 1-amino-2,3-propanediol, respectively (FIG. 2C). A keto-linked compound (i.e. where X is a direct linkage) may be prepared by condensation of aldehyde terminated PEG (prepared by mild oxidation of hydroxyl-terminated PEG) with, for example, the Grignard reagent of 1-bromo-2,3-propanediol acetonide (FIG. 2D), followed by oxidation to the ketone, under non-acidic conditions, and hydrolysis of the acetonide to the diol. In each case, the diol is then acylated as usual.

The terminus of the PEG oligomer not linked to the glycerol moiety α terminus; group Z above) is typically hydroxy or methoxy, but may be functionalized, according to methods known in the art, to facilitate attachment of various molecules to the neutral lipopolymer, and/or for use in targeting the liposomes to a particular cell or tissue type or otherwise facilitating drug delivery. Molecules to be attached may include, for example, proteins, peptides, saccharides, antibodies, or vitamins. Examples 2 and 3 describe steps in the preparation of α-functionalized lipopolymers following routes similar to those described above, but are prepared with commercially available PEG oligomers wherein the α terminus is substituted with a group, such as t-butyl ether or benzyl ether, which is readily converted to hydroxyl after synthesis of the lipid portion of the molecule. This terminus is then activated, in this case, by conversion to a p-nitrophenylcarbonate.

III. Liposome Pharmacokinetics

Figure 3A:
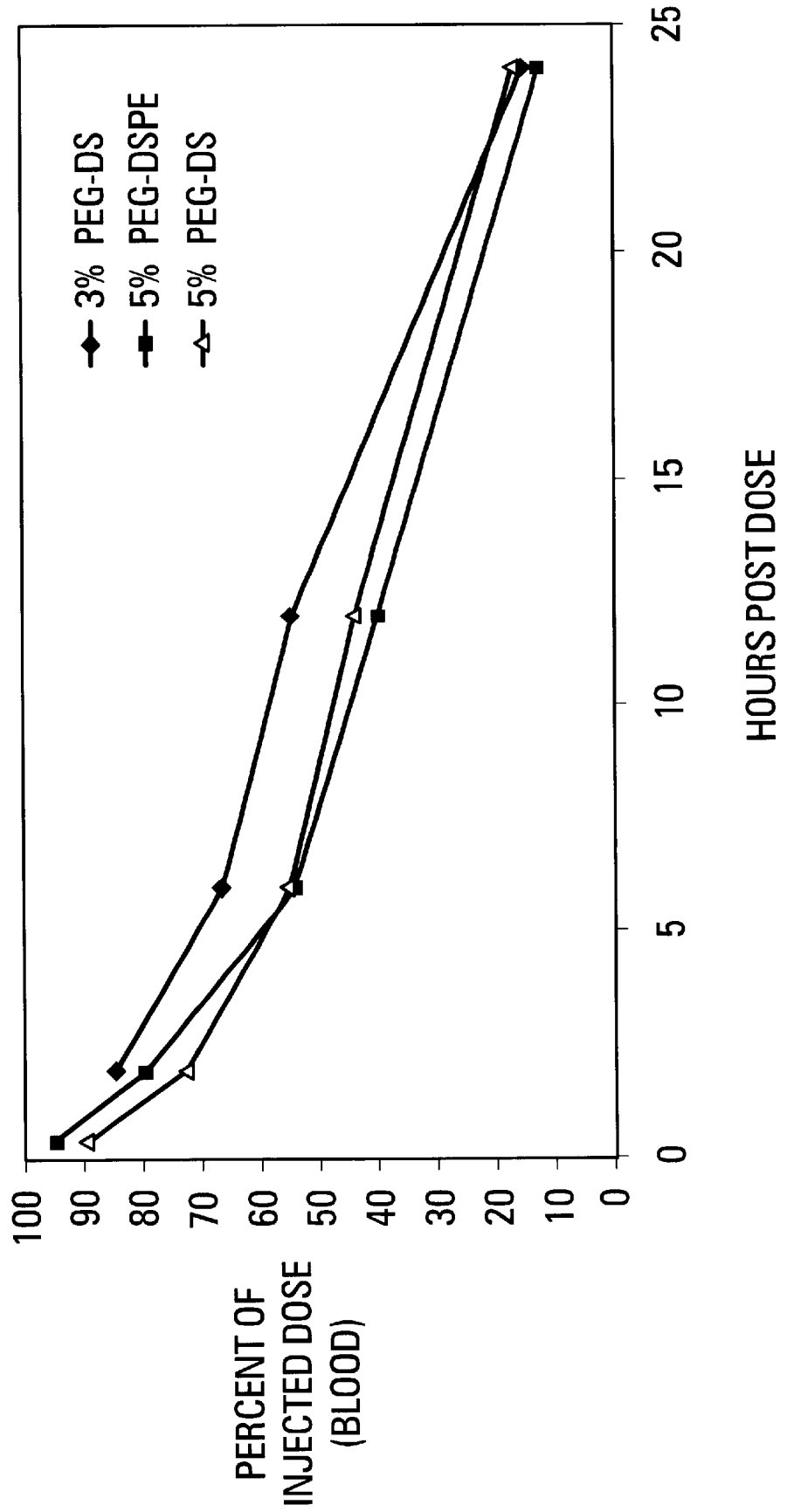
FIGS. 3A–3C are graphs showing the biodistribution of HSPC/Chol liposomes containing 3 mole percent PEG-c-DS (A); 5 mole percent PEG-DSPE (B); or 5 mole percent PEG-c-DS (C), in the blood, liver, and spleen.
Figure 3B:
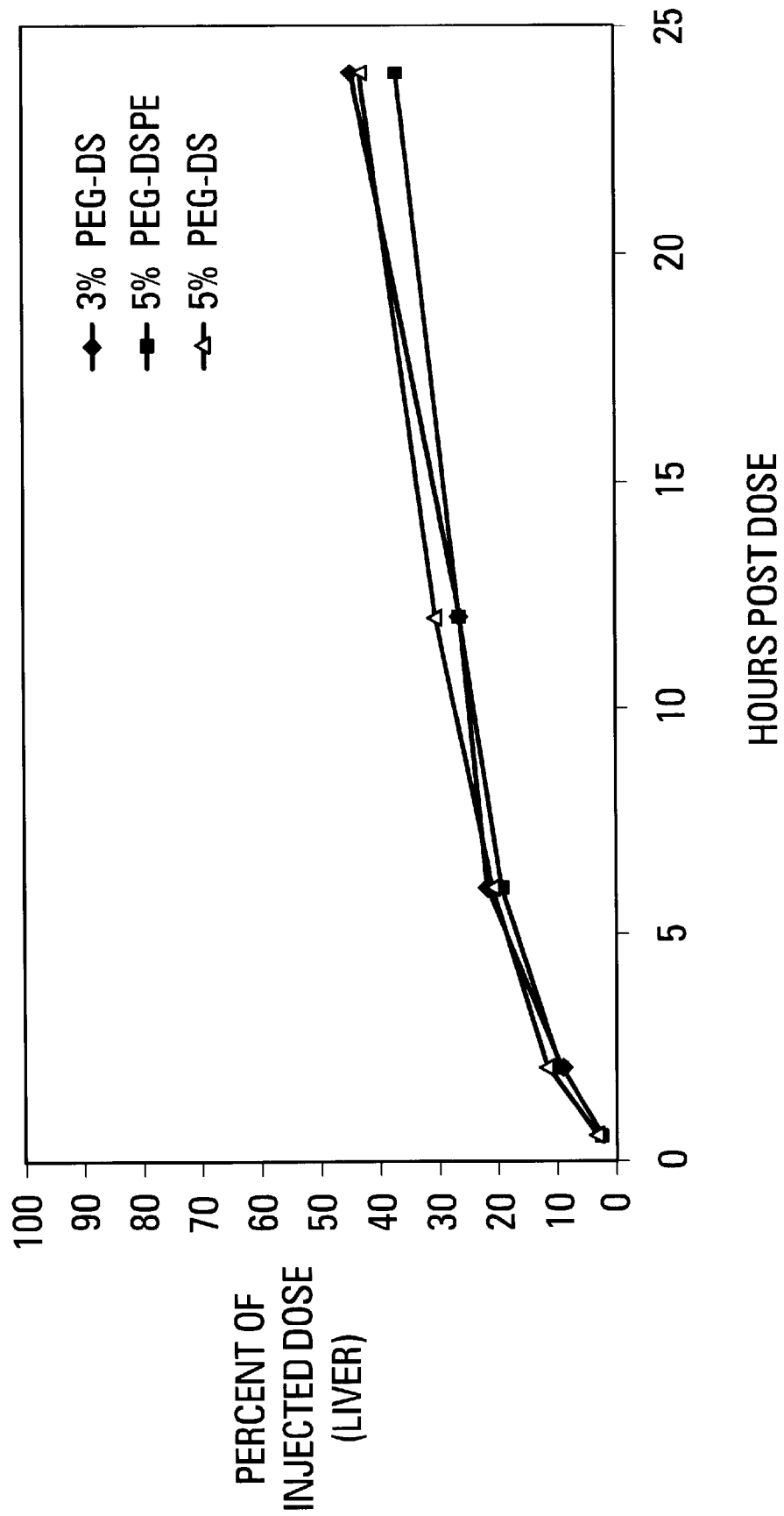
Figure 3C:
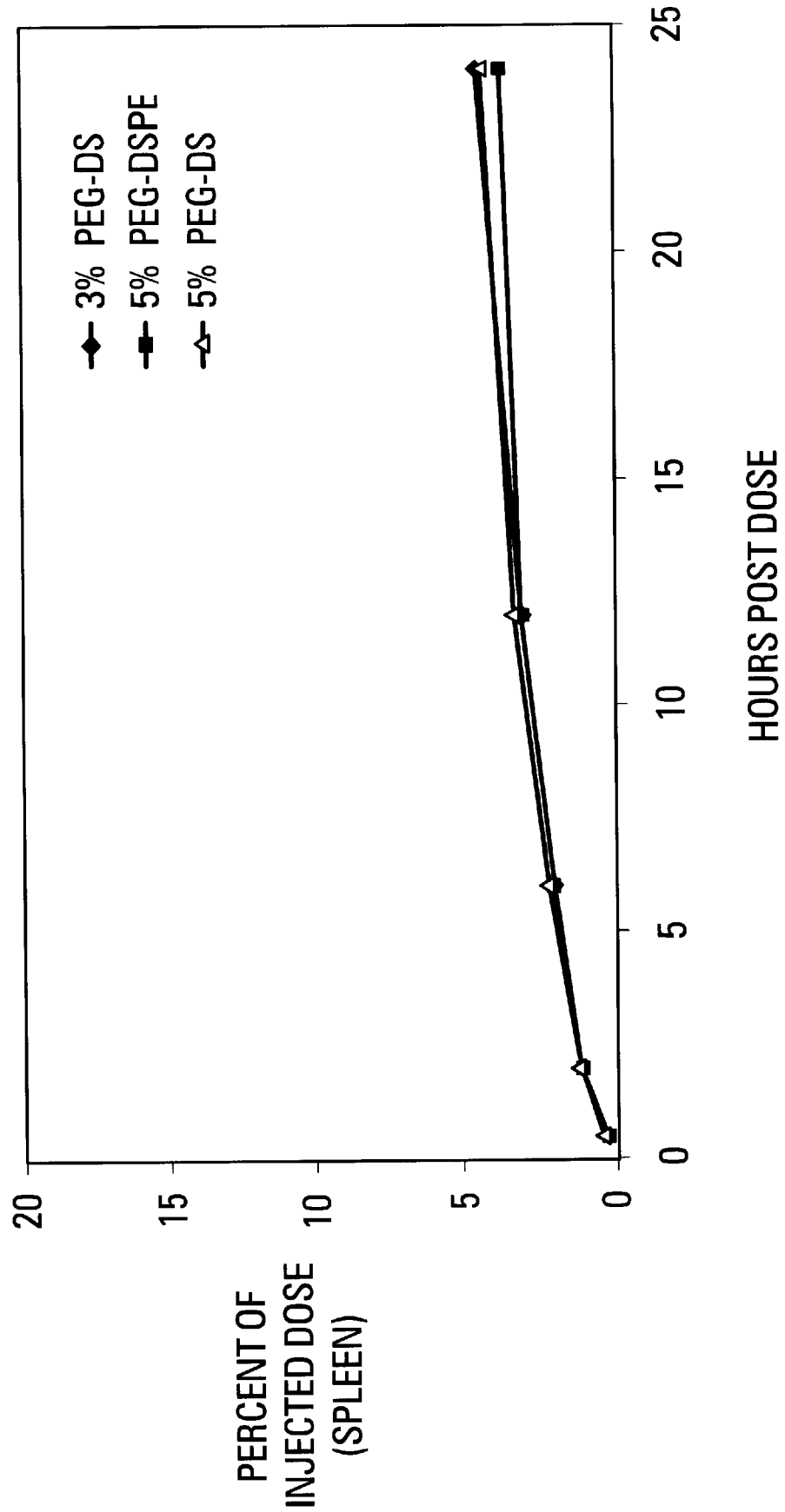

Long-circulating liposomes are formed by incorporating from about 1 to about 10 mole %, and more preferably from about 3 to about 6 mole %, of a neutral lipopolymer into liposomes composed of vesicle-forming lipids. To illustrate, liposomes incorporating from about 3 to about 5 mole % of either mpEG$_{2000}$-DSPE (distearoyl phosphatidyl ethanolamine) or carbamate linked lipopolymer, mPEG$_{2000}$-c-DS were prepared as described in Example 4. The balance of the lipids consisted of HSPC and cholesterol in a 1.5:1 mole ratio. The liposomes were loaded with the marker $^{125}$I-tyraminylinulin. A sample of each preparation was injected into the tail vein of mice, and the tissue distribution was determined at various time points, as described in Example 4. Levels present in the blood, liver and spleen are presented in Tables 1–3, and shown graphically in FIGS. 3A–3C. The data show the pharmacokinetics of the PEG-c-DS-containing liposomes were very similar to those of the liposomes containing PEG-DSPE.

TABLE 1

Liposome Distribution in Blood

| Time Point | % of Injected Dose | | |
|---|---|---|---|
| | A | B | C |
| 30 min | — | 94.8 ± 3.99 | 89.7 ± 6.94 |
| 2 h | 85.1 ± 1.99 | 79.8 ± 3.42 | 73.0 ± 17.4 |
| 6 h | 67.1 ± 6.25 | 54.5 ± 3.05 | 55.3 ± 2.51 |
| 12 h | 54.9 ± 6.04 | 39.7 ± 2.52 | 44.4 ± 2.52 |
| 24 h | 14.8 ± 2.81 | 12.4 ± 2.34 | 16.6 ± 2.38 |

TABLE 2

Liposome Distribution in Liver

| Time Point | % of Injected Dose | | |
|---|---|---|---|
| | A | B | C |
| 30 min | — | 2.27 ± 0.13 | 3.14 ± 0.95 |
| 2 h | 8.76 ± 2.01 | 9.42 ± 1.24 | 11.7 ± 1.74 |
| 6 h | 21.7 ± 2.55 | 19.3 ± 1.37 | 20.8 ± 0.86 |
| 12 h | 26.6 ± 0.51 | 26.4 ± 1.99 | 30.4 ± 1.28 |
| 24 h | 43.9 ± 2.7 | 36.6 ± 2.25 | 42.6 ± 0.48 |

TABLE 3

Liposome Distribution in Spleen

| Time Point | % of Injected Dose | | |
|---|---|---|---|
| | A | B | C |
| 30 min | — | 0.09 ± 0.06 | 0.23 ± 0.08 |
| 2 h | 0.96 ± 0.16 | 0.99 ± 0.09 | 1.08 ± 0.09 |
| 6 h | 1.94 ± 0.07 | 1.96 ± 0.29 | 2.12 ± 0.13 |
| 12 h | 3.15 ± 0.31 | 3.13 ± 0.12 | 3.35 ± 0.22 |
| 24 h | 4.69 ± 0.37 | 3.91 ± 0.31 | 4.56 ± 0.29 |

Figure 4:
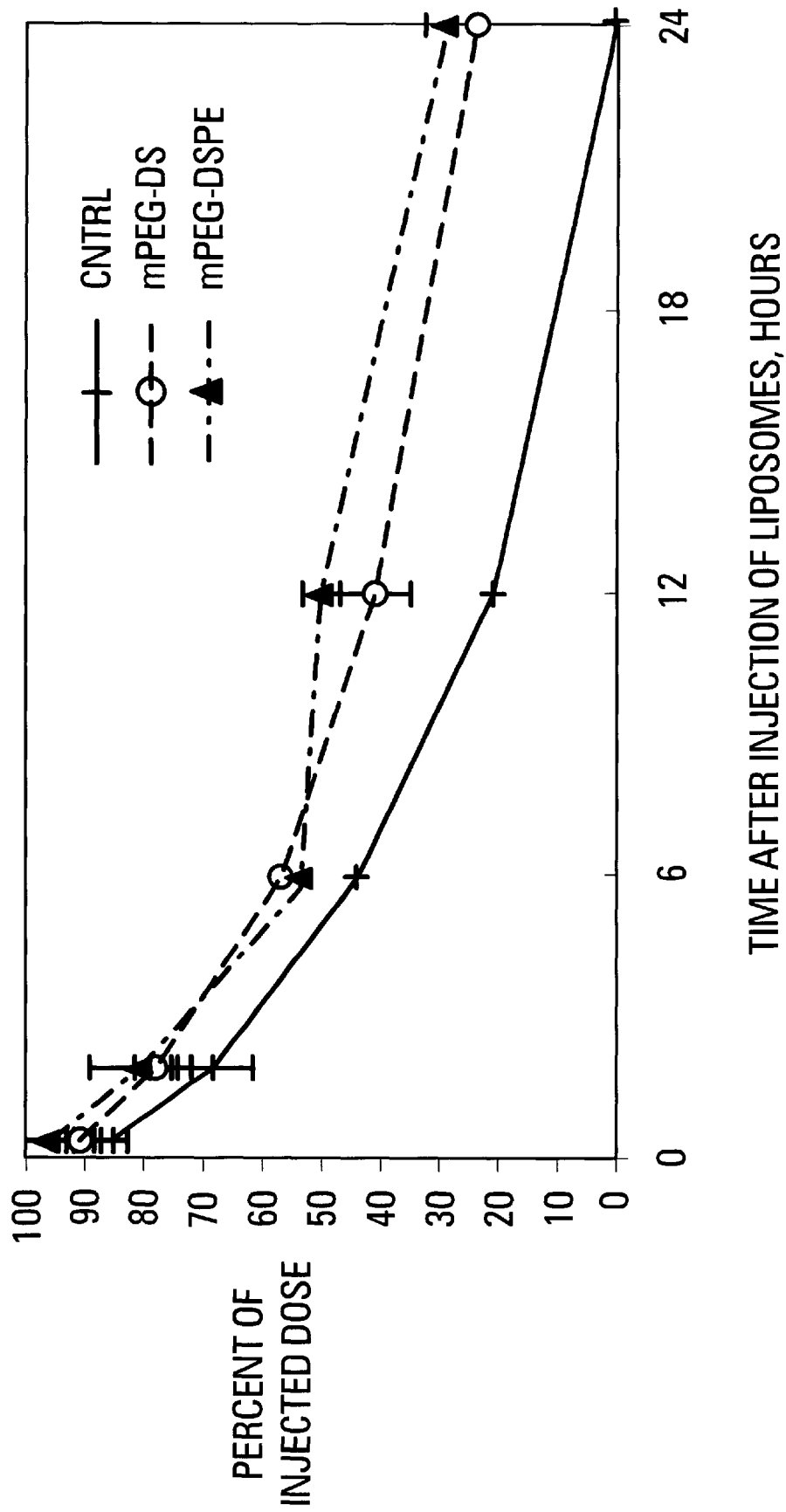
FIG. 4 is a graph showing the retention in the blood of 2:1 HSPC PEG free liposomes (crosses), i.e., no PEG, 5 mole percent PEG-DSPE (triangles), and 5 mole percent PEG-c-DS (circles)
Figure 5:
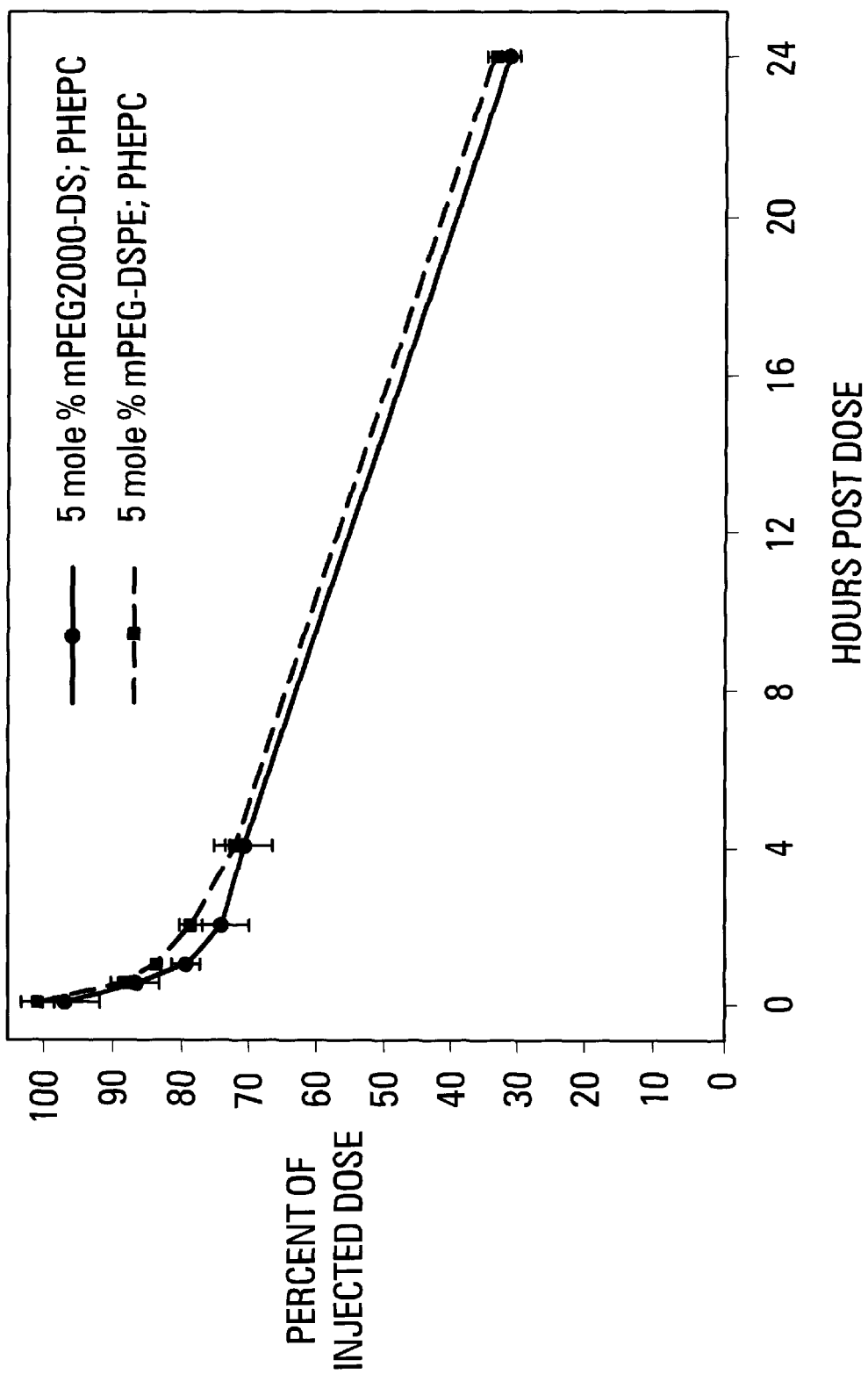
FIG. 5 is a graph showing the retention in the blood of PHEPC liposomes containing 5 mole percent PEG-c-DS (circles) and 5 mole percent PEG-DSPE (squares).

A similar study compared the performance of both PEG lipids against a control formulation containing no PEG lipid. FIG. 4 shows the retention in the blood of 2:1 HSPC liposomes containing no PEG lipid (crosses), 5 mole % PEG$_{2000}$-DSPE (triangles), or 5 mole % PEG$_{2000}$-c-DS (circles).

Further studies were performed using liposomes containing mPEG$_{2000}$-c-DS: PHPC: Chol in a 5:55:40 molar ratio. The liposomes were labeled by incorporation of an indium-DTPA complex. Percent of injected dose was determined in the blood and in various tissues at 24 hours. The results are shown in Tables 4–6. Again, the liposomes showed typical long-circulating pharmacokinetics, with an average retention of greater than 70% of the injected dose after 4 hours, and greater than 30% after 24 hours.

TABLE 4

Percent of Injected Dose of Indium in Blood

| Animal # | 0.0 hrs | 0.5 hrs | 1.0 hrs | 2.0 hrs | 4.0 hrs | 24 hrs |
|---|---|---|---|---|---|---|
| Rat 1 | 103.7 | 91.2 | 82.5 | 73.8 | 72.0 | 33.1 |
| Rat 2 | 97.7 | 87.7 | 79.4 | 78.7 | 74.4 | 30.7 |
| Rat 3 | 95.1 | 83.1 | 77.8 | 68.6 | 64.4 | 29.8 |
| Rat 4 | 91.9 | 85.4 | 78.5 | 75.6 | 72.6 | 33.2 |
| Average | 97.1 | 86.8 | 79.6 | 74.2 | 70.9 | 31.7 |
| Std. Dev. | 5.0 | 3.4 | 2.1 | 4.2 | 4.4 | 1.7 |

TABLE 5

Percent of Injected Dose in Tissues at 24 Hours

| Tissue | Rat #1 | Rat #2 | Rat #3 | Rat #4 | Average | Std. Dev. |
|---|---|---|---|---|---|---|
| Liver | 7.5 | 6.9 | 6.7 | 7.2 | 7.1 | 0.3 |
| Spleen | 4.9 | 5.4 | 5.6 | 4.8 | 5.2 | 0.4 |
| Heart | 0.4 | 0.5 | 0.5 | 0.6 | 0.5 | 0.1 |
| Kidneys | 1.2 | 1.2 | 1.0 | 1.2 | 1.1 | 0.1 |
| Lung | 0.7 | 0.7 | 0.7 | 0.8 | 0.7 | 0.1 |
| Skin | 0.1 | 0.3 | 0.2 | 0.2 | 0.2 | 0.1 |
| Bone | 0.3 | 0.2 | 0.2 | 0.2 | 0.2 | 0.2 |

TABLE 5-continued

Percent of Injected Dose in Tissues at 24 Hours

| Tissue | Rat #1 | Rat #2 | Rat #3 | Rat #4 | Average | Std. Dev. |
|---|---|---|---|---|---|---|
| Muscle | 0.1 | 0.1 | 0.1 | 0.2 | 0.1 | 0.4 |
| Urine | 11.2 | 13.4 | 5.7 | 12.3 | 10.7 | 3.4 |

TABLE 6

Percent of Injected Dose Per Gram in Tissues at 24 Hours

| Tissue | Rat #1 | Rat #2 | Rat #3 | Rat #4 | Average | Std. Dev. |
|---|---|---|---|---|---|---|
| Liver | 0.7 | 0.7 | 0.7 | 0.7 | 0.7 | 0.3 |
| Spleen | 7.3 | 6.9 | 8.2 | 5.9 | 7.1 | 0.9 |
| Heart | 0.5 | 0.5 | 0.5 | 0.5 | 0.5 | 0.4 |
| Kidneys | 0.6 | 0.6 | 0.5 | 0.6 | 0.6 | 0.6 |
| Lung | 0.6 | 0.5 | 0.5 | 0.6 | 0.5 | 0.6 |
| Skin | 0.1 | 0.1 | 0.1 | 0.1 | 0.1 | 0.1 |
| Bone | 0.4 | 0.4 | 0.4 | 0.4 | 0.4 | 0.3 |
| Muscle | 0.1 | 0.1 | 0.1 | 0.1 | 0.1 | 0.2 |
| Urine* | 0.6 | 0.6 | 0.3 | 0.8 | 0.6 | 0.2 |

*Percent of injected dose per mL.

Finally, liposomes containing 5 mole % $mPEG_{2000}$-c-DS or $mPEG_{2000}$-DSPE and the remainder PHEPC, were compared with respect to percent remaining in the blood up to 24 hours post administration. As shown in FIG. 4, the pharmacokinetics were virtually identical, with approximately 40% retention after 24 hours.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The following Examples illustrate but are not intended in any way to limit the invention.

EXAMPLE 1A

Synthesis of mPEG-c-DS (mPEG Aminopropanediol Distearoyl; α-Methoxy-ω-2,3-di (stearoyloxy)propylcarbamate Poly(ethylene Oxide))

A solution of $mPEG_{2000}$ (20 g, 10 mol) was azeotropically dried in toluene (50 mL, 120° C.). After the temperature of the above solution reached 25° C., it was treated with nitrophenyl chloroformate (3.015 g, 15 mol) followed by TEA (2.01 mL, 15 mol). This mixture was allowed to react for 1½ hr. The TEA-salt was filtered and the solvent removed to give crude $mPEG_{2000}$-nitrophenylchloroformate, to which a solution of aminopropanediol (3 g, 30 mol) in acetonitrile (50 mL) was added. This mixture was stirred overnight at room temperature. The insolubles were removed by filtration and the solvent was evaporated. The product was recrystallized twice from isopropanol. Yield: 13.7 g, 65%. $^1$HNMR: (300 MHz, DMSO-$D_6$) δ 3.23 (s, $OCH_3$, 3H), 3.65 (s, PEG, 180H), 4.05 (t, urethane $CH_2$, 2H), 4.42 (t, 1° OH, 1H), 4.57 (d, 2° OH, 1H).

The product, $mPEG_{2000}$ aminopropanediol (2.3 g, 1.08 mol, 2.17 meq of OH), was dissolved in toluene (30 mL) and azeotropically dried, removing about 10 mL, of the solution. The solution was allowed to cool to room temperature. Pyridine (4 mL, 20%) was added by pipette, followed by addition of stearoyl chloride (1 g, 4.3 mol). Immediately a white precipitate was formed. The reaction mixture was refluxed overnight at 120° C. and allowed to cool. When the temperature of the reaction flask reached about 40° C., the pyridine salt was filtered. The filtrate was evaporated. The product ($PEG_{2000}$-c-DS) was purified by recrystallizing twice from isopropanol (2×30 mL) and dried in vacuo over $P_2O_5$.

Yield: 2.26 g, 80%. TLC (chloroform:methanol, 90:10): mPEG aminopropanediol $R_f$=0.266; PEG-c-DS $R_f$=0.533. $^1$HNMR: (300 MHz, DMSO-$D_6$) δ 0.89 (t, $CH_3$, 6H), 1.26 (s, $CH_2$, 56H), 1.50 (2t, $2CH_2$, 4H), 2.24 (t, $CH_2\underline{CH_2}$ C=O, 4H), 3.23 (s, $OCH_3$, 3H), 3.50 (s, PEG, 180H), 4.00 (dd, $CH_2$ of APD, 1H), 4.02 (t, $CH_2$OC=O—N, 2H), 4.20 (dd, $CH_2$ of APD, 1H), 4.98 (M, CHOC(O), 1H), 7.34 (m, NH, 1H).

A similar procedure was used to prepare mPEG-c-DS using mPEG polymers of molecular weight 750, 5000, and 12000. The structures were verified by $^1$H-NMR and mass spectrometry. Molecular weights as determined by MALDI (Matrix Assisted Laser Desorption/Ionization) are given below:

| Conjugate | MW by MALDI |
|---|---|
| mPEG(750)-c-DS | 1426 |
| mPEG(2000)-c-DS | 2892 |
| mPEG(5000)-c-DS | 5816 |
| mPEG(12000)-c-DS | 12729 |

EXAMPLE 1B

Synthesis of PEG-c-DE (mPEG Aminopropanediol Diecosanoyl α-Methoxy-ω)-2,3-di(ecosanoyloxy) propylcarbamate Poly(ethylene oxide))

In a 100 ml round bottom flask, ecosanoic acid (500 mg, 1.6 mmol) was dissolved in toluene (20 ml) and oxalyl chloride (147 μl, 1.68 mmol) was added by pipette. To the stirring reaction, 1% DMF was added. Upon addition of DMF, gas was released. All contact with this gas must be avoided. After 10 minutes, the toluene was evaporated, and an additional 20 ml of toluene was added and evaporated to remove any excess of oxalyl chloride. The residue was redissolved in 10 ml of toluene. mPEG-aminopropanediol, prepared as described above, (1.19 g, 0.56 mmol) was added to the solution, a reflux condenser was attached, and the mixture was refluxed overnight. Analysis by TLC (methanol and chloroform, 9:1) showed the reaction to be complete. After the reaction mixture cooled, the undissolved material was filtered, and the filtrate was taken to dryness. The product was purified by recrystallizing three time from isopropanol and dried in vacuo over $P_2O_5$. Yield: 1.0 mg, 70%. $^1$HNMR: (360 MHz, DMSO-$D_6$) δ 0.89 (t, $CH_3$, 6H), 1.26 (s, $CH_2$, 66 H of lipid), 1.50 (t, $2CH_2$, 4H), 2.24 (t, $CH_2$ $\underline{CH_2}$ C=O, 4H), 3.23 (s, $OCH_3$, 3H), 3.50 (s, PEG, 180H), 4.00 (dd, $CH_2$ of APD, 1H), 4.05 (t, $CH_2{}^j\underline{CH_2}$C+O, 4H), 3.23 (s, $OCH_3$, 3H, 3.50 (s, PEG, 180H), 4.00 (dd, $CH_2$ of APD, 1H), 4.05 (t, $CH_2$OC=O—N, 2H), 4.20 (dd, $CH_2$ of APD, 1H), 4.98 (m, CHOC(O), 1H), 7.34 (m, NH, 1H) ppm.

EXAMPLE 2

Preparation of t-Bu-O-PEG-Aminopropanediol via t-Bu-O-PEG-O-Succinimide

A. t-Bu-O-PEG-O-Succinimide tBu-O-PEG-2000 from Polymer Labs (10 g, 5 mmol) was azeotropically dried by dissolving in 120 mL toluene and removing about 20 mL of the solvent, collecting any water in a Dean Stark trap.

The solution was cooled to room temperature, and phosgene (15 ml) was added. The mixture was allowed to react overnight at room temperature. After the completion of the reaction, the solvent was removed by rotary evaporator. About 50 ml of fresh toluene was added and removed by rotary evaporator. The residue was dissolved in dry toluene (30 ml) and methylene chloride (10 ml). To this solution, N-hydroxysuccinimide (1.7 g, 14.8 mmol) and triethylamine (2.1 ml, 14.9 mmol) were added, and the mixture was allowed to react overnight at room temperature, after which time the reaction was complete by TLC.

| Compound | $R_f$ (CHCl$_3$: CH$_3$OH, 90:10) |
|---|---|
| t-Bu-O-PEG-OH | 0.44 |
| t-Bu-O-PEG-OSc | 0.51 |

The salt was filtered from the reaction mixture, the solvent was removed by evaporation, and the solid was recrystallized twice from isopropyl alcohol and dried over $P_2O_5$. Yield: 9.2, 85%. $^1$HNMR: (CDCl$_3$, 360 MHz) δ 1.25 (s, t-Bu, 9H), 2.82 (s, CH$_2$CH$_2$, 4H), 3.60 (s, PEG, 180 H), 4.45 (t, CH$_2$OCONH, 2H) ppm.

B. t-Bu-O-PEG-Aminopropanediol

To a solution of aminopropanediol (300 mg, 3.2 mmol) in DMF (10 ml), t-Bu-PEG-OSc (5 g, 2.29 mmol) was added and allowed to react overnight. All NHS ester was consumed, giving a mixture showing one spot on TLC.

| Compound | $R_f$ (CHCl$_3$: CH$_3$OH, 90:10) |
|---|---|
| t-Bu-O-PEG-OSc | 0.51 |
| t-Bu-O-PEG-APD | 0.35 |

A previously washed acidic ion exchange resin (~1 g) was added to the reaction mixture and removed by filtration after 30 minutes. The solvent was removed and the residue recrystallized from 200 mL of isopropyl alcohol. The solid was collected and dried over $P_2O_5$. Yield: 4.2 g, 85%. $^1$HNMR: (D6-DMSO, 360 MHz) δ 1.25 (s, t-Bu, 9H), 3.68 (s, PEG, 180 H), 4.03 (t, CH$_2$OCONH, 2H), 4.43 (t, 1° OH, 1H), 4.55 (d, 2° OH, 1H), 6.98 (t, NH, 1H) ppm.

EXAMPLE 3

Preparation of p-Nitrophenylcarbonate-PEG-c-DS

A. Bn-O-PEG-Nitrophenylcarbonate (NPC)

Bn-O-PEG-2000 from Shearwater Polymers (Huntsville, La.; 5 g, 2.41 mmol) was azeotropically dried by dissolving in 120 mL toluene and removing about 20 mL of the solvent, collecting any water in a Dean Stark trap. The solution was cooled to room temperature and remaining solvent was evaporated under reduced pressure.

The residue was dissolved in 30 ml of methylene chloride/ethyl acetate (60:40), and p-nitrophenylchloroformate (729 mg, 3.6 mmol) and triethylamine (1 ml, 7.2 mmol) were added. The reaction was carried out at 4° C. for 8–16 hours. This method slows down the reaction but eliminates the formation of bis PEG-carbonate. A UV visible spot on GF silica plate indicated the completion of the reaction.

The reaction mixture was treated with previously cleaned acidic and basic ion exchange resin for 30 minutes, filtered, and taken to complete dryness. The product was recrystallized from isopropyl alcohol and dried over $P_2O_5$. Yield: 4.4 g, 80%.

B. Bn-O-PEG-Aminopropanediol

To a solution of aminopropanediol (260 mg, 1.9 mmol) in DMF (10 ml), Bn-O-PEG-NPC, as prepared above (4.3 g, 2.9 mmol), was added and reacted for 5 hours. All Bn-O-PEG-NPC was consumed, the reaction mixture giving one spot on TLC (chloroform:methanol:water 90:18:2).

The reaction mixture was treated with 5 g previously cleaned acidic ion exchange resin for 30 minutes, filtered, and taken to complete dryness. The product was recrystallized from isopropyl alcohol and dried over $P_2O_5$. Yield: 3.8 g, 91%.

C. Bn-O-PEG-c-Distearoyl

A solution of Bn-O-PEG-aminopropanediol (3 g, 1.36 mmol), stearic acid (1.94 g, 6.79 mmol), and DPTS (4-(dimethylamino)pyridinium 4-toluenesulfonate) as catalyst (408 mg, 1.36 mmol) was stirred at room temperature for 20 minutes. Diisopropylcarbodiimide (1.28 ml, 8.16 mmol) was added by pipette and the mixture allowed to react overnight. TLC (chloroform:methanol, 90: 10) showed complete reaction of the diol.

Basic ion exchange resin (~5 g) was added to the reaction mixture. After 30 minutes of shaking, the resin was filtered and the filtrate was taken to dryness. The residue was recrystallized from isopropanol (100 ml) and dried over $P_2O_5$. Yield: 4 g, 80%.

D. HO-PEG-c-Distearoyl

Two different approaches were taken for the deprotection of the benzyl group of Bn-O-PEG-c-DS.

Method 1. Hydrogenolysis: Deprotection by Palladium on Carbon. To a solution of Bn-O-PEG-c-DS (218 mg, 0.08 mmol) in 5 ml of methanol, 10% Pd/C (110 mg) and ammonium formate (107 mg, 0.8 mmol) were added and the mixture allowed to reacted at room temperature overnight. Pd/C was removed by filtration over Celite®, and the filtrate was taken to dryness. The residue was dissolved in chloroform and washed three times with saturated NaCl. The chloroform phase was collected, dried with MgSO$_4$, filtered and concentrated. The solid residue was lyophilized from tBuOH, and the resulting powder was dried over $P_2O_5$. Yield: 80%, 175 mg. Method 2. Deprotection by Titanium Tetrachloride. A solution of Bn-O-PEG-c-DS (1.18 g, 0.43 mmol) in methylene chloride (10 ml) was cooled in an ice bath for 5 minutes. Titanium tetrachloride (3 ml, 21.5 mol, excess) was transferred via an oven dried syringe into the sealed reaction flask. After 5 minutes, the ice bath was removed, and the deprotection reaction was carried out overnight at room temperature. Complete deprotection was shown by a lower shifted spot (relative to starting material) on a GF silica TLC plate.

About 40 ml of chloroform was added to the reaction mixture, and the mixture was transferred to a separatory funnel containing 40 ml of saturated NaHCO$_3$. The mixture was shaken gently (to avoid formation of an emulsion) and the chloroform layer was collected. This extraction was repeated 3 times, and the chloroform phase was collected and was extracted once more with a fresh portion of saturated NaHCO$_3$ to ensure complete removal of TiCl$_4$. The collected chloroform phase was dried with MgSO$_4$, filtered and concentrated.

The above residue was dissolved in 1 ml of chloroform and added to a prepared column of silica gel (200–400 mesh, 60 Å). The polarity of the mobile phase (chloroform) was increased by 2% incremental additions of methanol until the product eluted at 10% methanol/90% chloroform. The product was collected and the solvent removed by rotary evaporator. The solid was lyophilized from tBuOH and dried over $P_2O_5$. Yield: 70%, 800 mg.

E. p-Nitrophenylcarbonate-PEG-c-DS

The reaction flask, stirring bar, syringes and starting material (HO-PEG-c-DS, as prepared above) were meticulously dried before start of the reaction.

To a solution of HO-PEG-c-DS (1.2 g, 0.45 mmol) in 10 ml of methylene chloride/ethyl acetate (60:40), p-nitrophenylcarbonate (136 mg, 0.65 mmol) and triethylamine (188 μl, 1.35 mmol) were added. The reaction was carried out at 4° C. (to eliminate the formation of bisPEG-carbonate) for 8–16 hours, after which time the reaction was complete by GF silica gel TLC.

| Compound | $R_f$ (CHCl$_3$: CH$_3$OH, 90:10) |
|---|---|
| HO-PEG-c-DS | 0.40 |
| NPC-PEG-c-DS | 0.54 |

The reaction mixture was treated for 30 minutes with previously cleaned acidic and basic ion exchange resins and filtered. The filtrate was taken to complete dryness and the residue recrystallized from isopropyl alcohol. The solid was dried over $P_2O_5$. Yield: 70%. $^1$NHMR: (D6-DMSO, 360 MHz) δ 0.86 (t, CH$_3$, 6 H), 1.22 (s, DS, 56H), 1.48 (m, CH$_2$CH$_2$(CO)), 4H), 2.26 (2 xt, CH$_2$OCONH, 2H), 4.03 & 4.22 (2×d, CH$_2$CH of lipid, 2H), 4.97 (M, CHCH$_2$ of lipid), 6.98 (t, NH, 1H), 7.55% 8.32 (2×d, aromatic, 4H) ppm.

EXAMPLE 4

Preparation and Biodistribution Studies of PEG-DSPE- and PEG-c-DS- Containing Liposomes Lipid films were formed, by dissolution and removal of solvent, from mixtures of HSPC:Chol:PEG lipid in the following ratios:

A: 58:39:3; PEG lipid=PEG-c-DS
B: 57:38:5; PEG lipid=PEG-DSPE
C: 57:38:5; PEG lipid=PEG-c-DS The films were hydrated in freshly prepared $^{125}$I-Tyraminylinulin in 25 mM HEPES containing 140 mM NaCl, pH 7.4, and extruded to form liposomes 100–105 nm in diameter. The liposomes were sterilized by filtration through 0.22 μm Millipore (Millipore Corporation, Bedford, Mass.) low protein-binding syringe-end filters. Aliquots were counted to determine the injection counts of $^{125}$I. Lipid concentrations were determined by assaying the phosphate content of the liposome preparations, and the liposome preparations were diluted in sterile buffer to a final concentration of 2.5 μmol/mL. Mice were injected iv via the tail vein with 0.2 mL of the diluted liposomes, so that each mouse received 0.5 μmol of phospholipid. At the various time points, mice were euthanised by halothane anesthesia followed by cervical dislocation, the blood sampled by cardiac bleeds, and the blood and various organs assayed for $^{125}$I counts.

It is claimed:

1. A liposomal composition comprising about 1 mole percent to about 10 mole percent of a neutral lipopolymer having the formula:

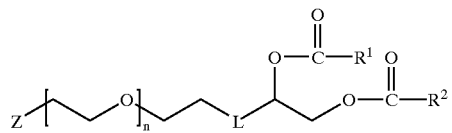

where
each of $R^1$ and $R^2$ is an alkyl or alkenyl chain having between about 8 to about 24 carbon atoms;
n=about 10 to about 300,
Z is selected from the group consisting of hydroxy, alkoxy, benzyloxy, carboxylic ester, sulfonic ester, alkyl or aryl carbonate, amino, and alkylamino; and
L is selected from the group consisting of (i) —X—(C═O)—Y—CH$_2$—, (ii) —X—(C═O)—, and (iii) —X—CH$_2$—, where X and Y are independently selected from oxygen, NH, and a direct bond, with the proviso that when L is —X—(C═O)—, X is not NH; and the remainder vesicle-forming lipids.

2. The composition of claim 1, where X is oxygen and Y is nitrogen.

3. The composition of claim 1, where L is a carbamate linkage, an ester linkage, or a carbonate linkage.

4. The composition of claim 3, wherein L is —O—(C═O)—N—CH$_2$— (a carbamate linkage).

5. The composition of claim 1, where Z is hydroxy or methoxy.

6. The composition of claim 1, comprising about 3 mole percent to about 6 mole percent of the neutral lipopolymer.

7. The composition of claim 1, where each of $R^1$ and $R^2$ is an unbranched alkyl or alkenyl chain having between about 8 to about 24 carbon atoms.

8. The composition of claim 6, wherein each of $R^1$ and $R^2$ is $C_{17}H_{35}$.

9. The composition of claim 1, where n is between about 20 and about 115.

10. A method of increasing circulation time of a liposome comprising vesicle-forming lipids, said method comprising incorporating in said liposome, with said vesicle-forming lipids, about 1 mole percent to about 10 mole percent of a neutral lipopolymer having the formula:

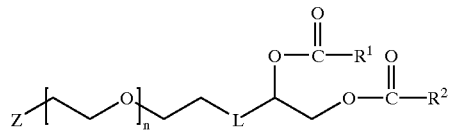

where
each of $R^1$ and $R^2$ is an alkyl or alkenyl chain having between about 8 to about 24 carbon atoms;
n=about 10 to about 300,
Z is selected from the group consisting of hydroxy, alkoxy, benzyloxy, carboxylic ester, sulfonic ester, alkyl or aryl carbonate, amino, and alkylamino; and
L is selected from the group consisting of (i) —X(C═O)—Y—CH$_2$—, (ii) —X—(C═O)—, and (iii) —X—CH$_2$—, where X and Y are independently selected from oxygen, NH, and a direct bond, with the proviso that when L is —X—(C═O)—, X is not NH.

11. The method of claim 10, where X is oxygen and Y is nitrogen.

12. The method of claim 10, where L is a carbamate linkage, an ester linkage, or a carbonate linkage.

13. The method of claim 12, wherein L is —O—(C=O)—N—CH$_2$— (a carbamate linkage).

14. The method of claim 10, where Z is hydroxy or methoxy.

15. The method of claim 10, wherein about 3 mole percent to about 6 mole percent of the neutral lipopolymer is incorporated.

16. The method of claim 10, where n is between about 20 and about 115.

* * * * *